United States Patent
Gavrilov et al.

(10) Patent No.: US 7,402,817 B2
(45) Date of Patent: Jul. 22, 2008

(54) SYSTEM AND METHOD FOR CROSS-TALK CANCELLATION IN A MULTILANE FLUORESCENCE DETECTOR

(75) Inventors: Dmitri N. Gavrilov, Port Jefferson Station, NY (US); Boris Gorbovitski, Stony Brook, NY (US); Vera Gorfinkel, Stony Brook, NY (US); Georgiy Gudkov, Centereach, NY (US); Marina Tcherevishnik, Centereach, NY (US)

(73) Assignee: The Research Foundation of State University of New York, Stony Brook, NY (US)

( * ) Notice: Subject to any disclaimer, the term of this patent is extended or adjusted under 35 U.S.C. 154(b) by 0 days.

(21) Appl. No.: 11/627,146

(22) Filed: Jan. 25, 2007

(65) Prior Publication Data
US 2007/0194249 A1      Aug. 23, 2007

Related U.S. Application Data

(63) Continuation of application No. PCT/US2005/027059, filed on Jul. 29, 2005.

(60) Provisional application No. 60/592,170, filed on Jul. 29, 2004.

(51) Int. Cl.
*G01N 21/64* (2006.01)
(52) U.S. Cl. .................. 250/459.1; 250/458.1
(58) Field of Classification Search ............. 204/603, 204/601; 702/104; 250/458.1, 459.1, 252.1
See application file for complete search history.

(56) References Cited

U.S. PATENT DOCUMENTS

| 6,418,383 | B1 | 7/2002 | Wang |
| 6,539,323 | B2 | 3/2003 | Olson |
| 6,566,143 | B2 * | 5/2003 | Hoyt ..................... 436/172 |

OTHER PUBLICATIONS

Gavrilov et al., "Dynamic Range Of Fluorescence Detection And Base-Calling Accuracy In DNA Sequencer Based On Single-Photon Counting," Electrophoresis 2003, 24, 1184-1192.
Alaverdian et al., "A Family Of Novel DNA Sequencing Instruments Based On Single-Photon Detection," Electrophoresis 2002, 23, 2804-2817.
Yin et al., "Automatic Matrix Determination In Four Dye Fluorescence -Based DNA Sequencing," Electrophoresis 1996, 17, 1143-1150.

* cited by examiner

*Primary Examiner*—Constantine Hannaher
(74) *Attorney, Agent, or Firm*—Baker Botts LLP (57) ABSTRACT

The present invention is directed to a system and method for cross-talk cancellation for multi-lane fluorescence detectors. The invention may be implemented in accordance with a variety of systems, including systems for multi-capillary electrophoresis. The present invention is based on a special calibration procedure for determination of a channel cross-talk matrix and enables an accurate separation of the fluorescence emitted from individual capillary lanes. The proposed method for cross-talk calibration and removal is very useful for design and development of multi-lane single photon counting detection systems.

32 Claims, 2 Drawing Sheets

SYSTEM AND METHOD FOR CROSS-TALK CANCELLATION IN A MULTILANE FLUORESCENCE DETECTOR

CROSS-REFERENCE TO RELATED APPLICATIONS

This application is a continuation of International Application PCT/US05/27059, filed Jul. 29, 2005, which claims priority to U.S. Provisional Patent Application 60/592,170, filed on Jul. 29, 2004, which are hereby incorporated by reference in their entireties.

FIELD OF THE INVENTION

The present invention relates generally to photodetection systems and methods. More specifically, the present invention is directed to a system and method for cross-talk cancellation for multilane fluorescence detectors, such as those used in capillary electrophoresis for DNA sequencing.

BACKGROUND OF THE INVENTION

Capillary electrophoresis is a widely-used technique in high-throughput DNA sequencing. In practically all DNA sequencers, fluorescence labeling techniques are used for sequence detection. A number of extremely sensitive fluorescence detection techniques are available based on registering single photons, commonly referred to as the single photon detection (SPD) techniques. Such techniques are known in the prior art and are described in G. Papageorgas, H. Winter, H. Albrecht, et al., IEEE *Trans. on Instrumentation and Measurement*, 1999, Vol. 48, 6, pp. 1166-1177; Y. E. Tiberg and V. N. Paulauskas, *Instruments and Experimental Techniques*, 1981, Vol. 23, 5, pp. 1252-1255, A. M. Evtyushenkov, Y. F. Kiyachenko, G. I. Olefirenko and I. K. Yudlin, *Instruments and Experimental Techniques*, 1982, Vol. 24, 5, pp. 1265-1267, K. D. Shelevoi, *Instruments and Experimental Techniques*, 1985, Vol. 28, 3, pp. 614-616, the texts of which are fully incorporated herein by reference. Because of their complexity and cost, SPD techniques were mostly used for specialized scientific applications, as time resolved fluorescence spectroscopy or detection of single fluorescent molecules.

Recently, SPD techniques have been employed in single-lane DNA sequencing instruments, as documented in L. Alaverdian, S. Alaverdian, O. Bilenko, et al., I. Bogdanov, S. Domrachev, E. Filippova, D. Gavrilov, B. Gorbovitski, M. Gouzman, I. Gudkov, N. Lifshitz, S. Luryi, V. Ruskovoloshin, A. Stepukhovich, M. Tcherevishnik, G. Tyshko and V. Gorfinkel, Abstract Book of the conference "Advances in Genome Biology and Technology", p. 47, Marco Island, Fla., USA, Feb. 3-6, 2001; and L. Alaverdian, S. Alaverdian, O. Bilenko, I. Bogdanov, E. Filippova, D. Gavrilov, B. Gorbovitski, M. Gouzman, G. Gudkov, S. Domratchev, S. Kosobokova, N. Lifshitz, S. Luryi, V. Ruskovoloshin, A. Stepoukhovitch, M. Tcherevishnick, G. Tyshko, V. Gorfinkel, Electrophoresis 2002, 23, pp. 2804-2817 (hereinafter "Alaverdian et al."), the texts of which are fully incorporated herein by reference.

However, one of the most difficult challenges in the development of such systems is the elimination of the lane cross-talk caused by both optical and electronic cross-talk phenomena between channels of the single photon detector. The prior art systems have not addressed this issue.

There are two general types of lane cross-talk in single photon detection systems: optical and electronic. Electronic cross-talk may be caused by any multi-channel electronic module of a detection system, specifically as a result of, e.g., certain features of the electronic optics inside of a photo-multiplying tube. Optical cross-talk may be caused by, e.g., poor quality of a capillary array image on the receiving area of the photodetector, a contradiction between requirements of certain image magnification (from a lens) necessary for projection of the array as a whole onto the photodetector, and additional magnification of inner capillary volumes caused by capillary walls, a misalignment of the optical system after the capillary array placement, etc.

Cross-talk can be an especially significant problem in certain photodetection applications, such as, e.g., in DNA sequencing applications. Different lanes of a multi-lane DNA sequencer can have orders of magnitude variation in amplitude of fluorescent peaks. Accordingly, even very small lane cross-talk may cause ambiguity in data analysis.

Ultimately, some sources of channel cross-talk in a single photon detection system cannot be eliminated. Certain measures may be undertaken to reduce cross-talk, but these solutions are generally less efficient, more complex and expensive.

In prior art systems and methods, the general approach is to eliminate cross-talk, both optical and electrical, in the system. On the optical side, several strategies for removal of cross-talk have been employed. Examples include using an aperture mask to remove cross-talk at the input of the multi-capillary system, decreasing the distance of the collection system, and employing a smaller collection angle. However, while these measures may reduce or eliminate frond-end cross-talk, they also reduce the light collection efficiency. As a result, these cross-talk avoidance methods are limited in the types of equipment they may utilize, e.g., they may employ photodetectors which do not introduce cross-talk (even though these are typically the more sensitive and powerful photodetectors).

Accordingly, it is an object of the present invention to provide a novel system and method for calibration and elimination of channel cross-talk to enable an accurate separation of fluorescence signals emitted by individual capillaries.

SUMMARY OF THE INVENTION

In accordance with an exemplary embodiment of the present invention, a method is provided for reducing cross-talk in a multi-channel photodetection system, including the steps of determining a cross-talk matrix for the system; operating the system to detect data, and applying the cross-talk matrix to the detected data to reduce or remove channel cross-talk in the detected data.

In another exemplary embodiment of the present invention, a system is provided for reducing cross-talk in a photodetection system, the system including at least a processor and a memory, which memory stores instructions that may cause the processor to perform the steps of determining a cross-talk matrix, operating the system to obtain fluorescence data, and applying the cross-talk matrix to the fluorescence data to reduce cross-talk in the fluorescence data.

In another exemplary embodiment of the present invention, a system is provided for multi-capillary electrophoresis, the system including at least a light source, at least one multi capillary array positioned to receive light from the light source and filled with a material which produces a useful radiation caused by illumination with said laser source, a device for separating and identifying more than one spectral band of said useful radiation, a multi channel photodetector positioned to receive said useful radiation from the multi capillary array, a processor configured to receive data originating from the photodetector and, a memory coupled to the processor and containing instructions which, when executed by the processor, configure the processor to perform steps including determining a cross-talk matrix, operating the system to detect fluorescence data, and applying the cross-talk matrix to the fluorescence data to reduce cross-talk in the fluorescence data.

One of the important benefits of the present invention is that a much larger variety of equipment may be employed in designing multi-capillary systems. A larger collection angle may be utilized to provide a higher collection efficiency. Photodetectors that are more sensitive may be employed, even if they do introduce cross-talk into the system. Additionally, the light collection efficiency for a system according to the present invention may be much higher than in prior art systems. The approach thereby provides a system designer with substantially greater freedom in the selection of system components.

Throughout the Figures the same reference numerals and characters, unless otherwise stated, are used to denote like features, elements, components or portions of the illustrated embodiments. Moreover, while the present invention will now be described in detail with reference to the Figures, it is done so in connection with the illustrative embodiments.

DETAILED DESCRIPTION OF THE INVENTION

Figure 1:
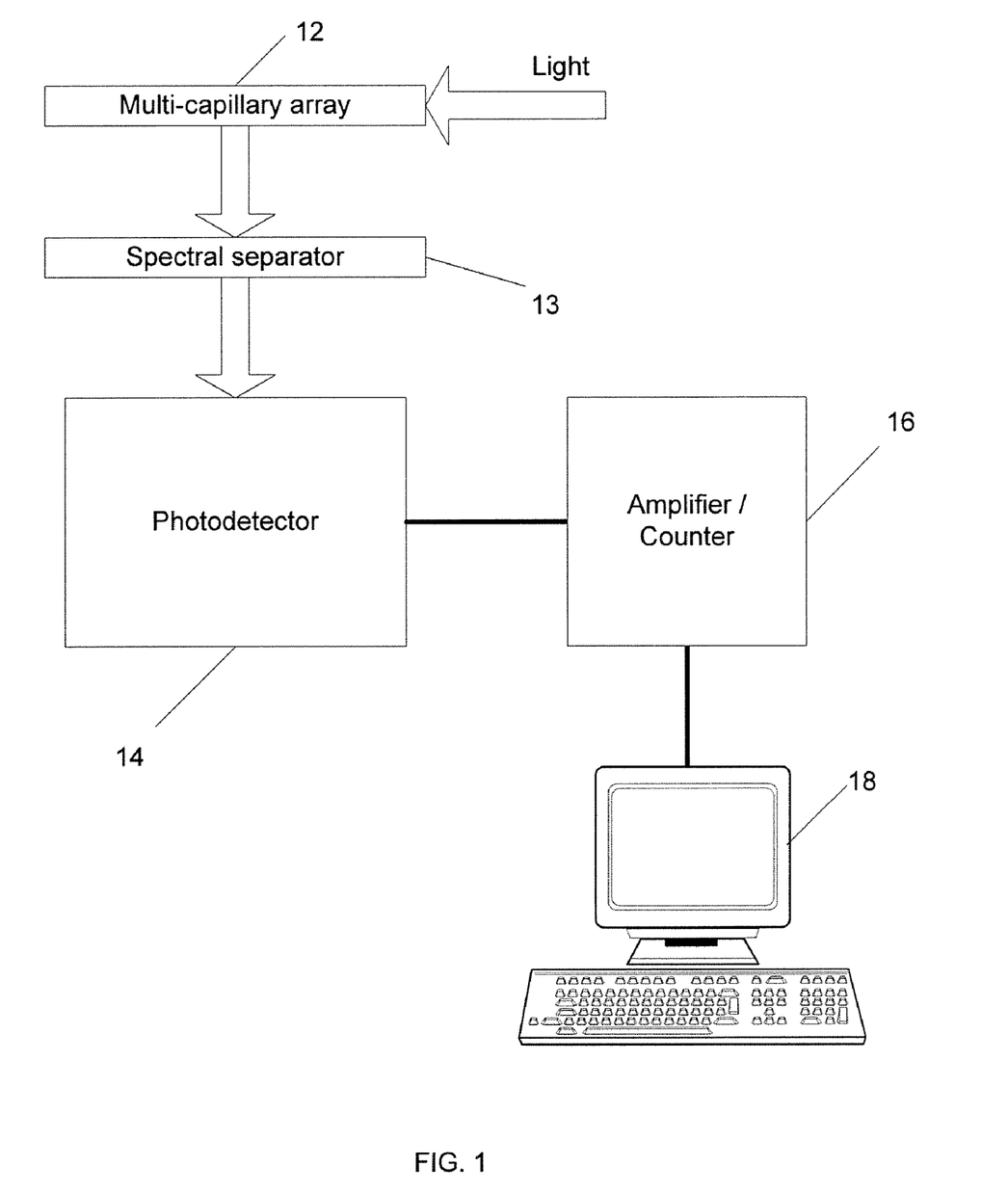
FIG. 1 is a block diagram illustrating an exemplary system according to the present invention.

Referring now to FIG. 1, an exemplary embodiment of a multi-lane DNA sequencing system according to the present invention is shown. In this exemplary embodiment, the system of FIG. 1 may be similar to the system described in Alaverdian et al. in with the exception of the novel lane cross-talk removal function implemented in accordance with the present invention.

The exemplary embodiment of FIG. 1 may include a multi-capillary array 12. In a preferred embodiment the array may be a 16- or 48-capillary array, such as those made available by Applied Biosystems, Inc., or may be any other multi-capillary array. The multi-capillary array 12 may preferably be inserted into a precision holder.

In accordance with the exemplary embodiment of FIG. 1, a laser beam illuminates the array from the side and excites fluorescence in the capillaries of the array 12. In an exemplary embodiment, the laser beam may be generated by a fiberized, single mode 25 mW NdYAG laser (532 mm), such as those available from Crystal Lasers, Inc. In order to illuminate the multi-capillary array from the side and excite fluorescence in all channels with high efficiency, an optical system comprising a collimator and microscope objective (JIS 10×/0.25) may be employed to reduce the beam size to a size of, e.g., 40 microns.

The fluorescence excited in the multi-capillary array is captured by a lens of a high numerical aperture, passed through a spectral separating device 13, and projected onto photosensitive pixels of a photodetector 14. In a preferred embodiment, the spectral separating device 13 may be a rotating filter wheel comprising four band pass filters passing the fluorescence in four different spectral bands. Such a device may be advantageously employed because the system cross-talk effects may differ in different spectral bands. The spectral separator device may isolate particular spectral bands for cross-talk analysis. Revolutions of the filter wheel may be synchronized with the photodetector 14 so that the photodetector is provided with information regarding what color light it is receiving at any given time. Although outside the scope of the present invention, various other optical filtering may be employed to ensure efficient transmission of the fluorescence excited in the multi-capillary array to the photodetector 14. For example, the lens may preferably be any lens with high numerical aperture, such as the commercially-available Canon EF 50 mm 1:1.4. The photodetector 14 may preferably be a 32-channel PMT, such as the H72060 developed by Hamamatsu. However, any photodetector and filtering apparatus may be employed in accordance with the present invention, as would be understood by one of ordinary skill in the art.

The photodetector 14 may preferably be operated in a single photon counting mode in accordance with this exemplary embodiment of the present invention. Each channel of photodetector 14 produces an output stream of short pulses in response to an input incident photon flux. The output pulses may generally range between 0.4-0.6 mA with corresponding peak voltage between 8 and 12 mV. In order to facilitate photon counting detection mode, a pulse amplifier and photon counter 16 may be employed. These functions may be performed using a single piece of hardware or several pieces of hardware, depending upon the particulars of the embodiment. For example, a 32-channel pulse amplifier and a 32-channel photon counter may be employed in accordance with the preferred embodiment.

The amplifier comprises 32 identical pulse amplifying channels with gain of 35-40 dB, bandwidth of 0.5-4,000 MHz and 32 fast comparators. These comparators have a rise and fall time of about 2 ns, which limits the minimum pulse width to approximately 4.5 ns. After amplification, a digitization (counting) of the amplified signal is performed by a home designed 32-channel photon counter. In order to synchronize the counter with the rotating 4-color filter wheel and to identify band-pass filters, we use a 2-bit Gray code from two sensors installed on the filter wheel. The change of the code word at the sensor outputs indicates the change of the filter in alignment. The counting of the input photon pulses in each of the 32 channels is performed by summation of pulses arriving to the channel input during the time intervals when a particular band-pass filter is in alignment with the photodetector.

Data collected by the counter is transferred to a computer device such as a personal computer using standard IEEE 1284 Parallel Port Interface or other standard computer interface. The data is transferred in samples using a binary format. One data sample is collected during one full revolution of the filter wheel. The frame consists of count values obtained in 4 fluorescence detection bands (4 color filters) for each of the 32 detection channels. The frames are sent in order of their generation, determined by the filter code on the wheel and the direction of its rotation. Each frame starts with a 6-byte header which includes the following fields: 1-byte counter type, 2-byte frame number, 1-byte color code (filter number) and a 2-byte counting period length. The frame number contains the number of the current frame. The number is incremented by 1 for each following frame thus forming a rising sequence with overflow. The frame numbers serve as synchronization marks and are used by the data processing software to find data frames in a continuous data stream. Frame numbers are also used for verification of data integrity and for finding errors introduced by interference in the transmission line. The duration of the counting period is measured in milliseconds and is represented by a 2-byte value. The time duration when the filter is "on" is measured separately for each filter and is used by processing software to calculate a photocount rate. The frame size is 105 bytes. During the normal operation of the system, when the filter wheel performs ~10 revolutions per second, the counter produces about 4200 bytes per second, which results in approximately 1.48 MB per hour.

A special software package operating on a personal computer or other computing device may perform the recording and the on-line visualization of the data transferred by the counter. The recorded data may preferably undergo a preprocessing which includes non-linearity compensation, smoothing and lane cross-talk removal. Further processing may include an automated base calling and assigning quality factor based on PHRED approach.

Figure 2:
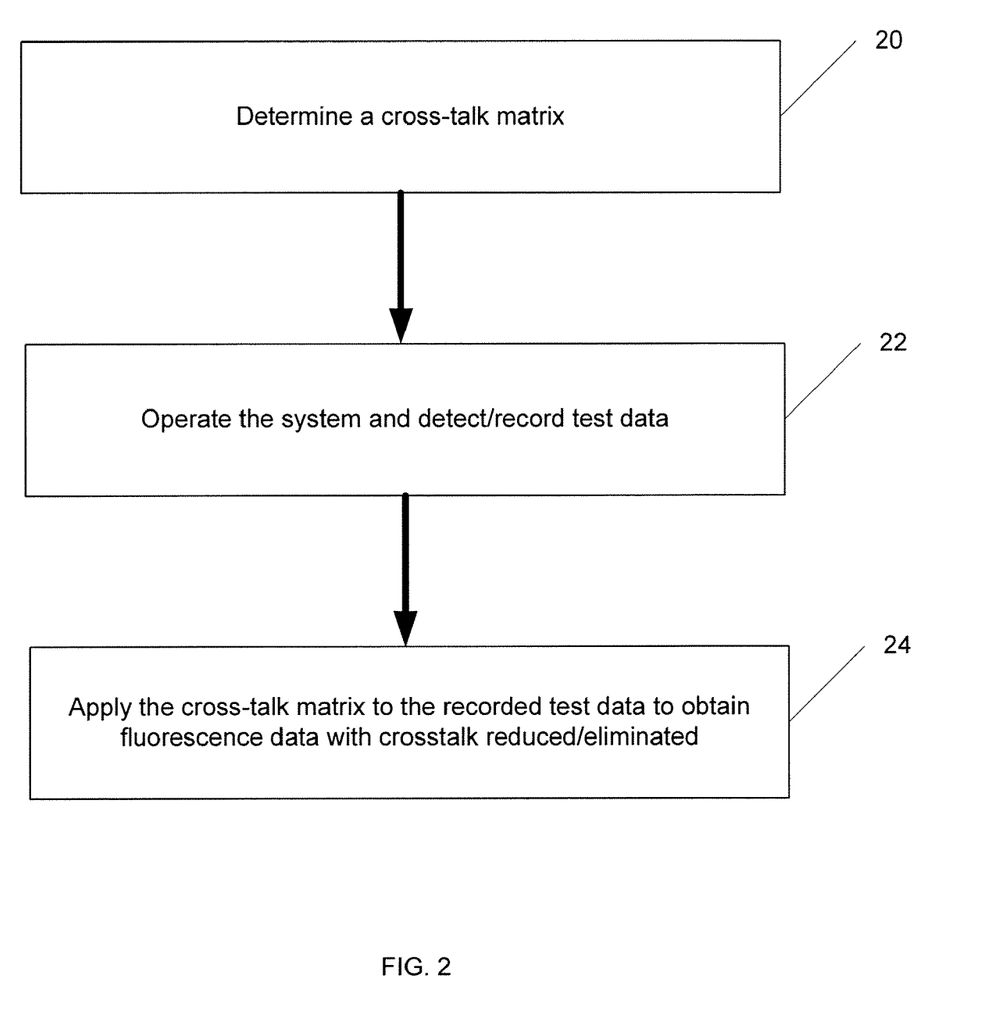
FIG. 2 is a flow diagram of a method in accordance with an exemplary embodiment of the present invention.

Referring now to FIG. 2, a flow diagram of an exemplary embodiment of the present invention is shown. As shown in FIG. 2, a first step 20 in the exemplary method is to determine a cross-talk matrix for a given system. Next, in step 22, the system is operated and fluorescence data recorded. Finally, in step 24, the cross-talk matrix is applied to the recorded test data to remove/eliminate cross-talk and leave only the correct fluorescence data measurements for each photodetector channel.

Notably, the details of all processing steps in accordance with the present invention are similar to those described in Alaverdian et al. with the exception of the novel cross-talk removal steps. One of the critical steps in the method according to the present invention is the determination of a cross-talk matrix for a given system, which cross-talk matrix may be used to remove unwanted cross-talk components from output data. Exemplary methods for determining a cross-talk matrix in accordance with the present invention are described herein below.

The proposed method of the cross-talk removal is based on the assumption that the fluorescence measurement system is linear, i.e., a photocount rate registered in the n-th channel of the photodetector is a sum of components contributed by signals in all other system channels and ratios of contributions from individual channels do not depend on the photocount rate. Linearity of optical cross talk is obvious as long as the measured photocount rate stays within the linear range of the PMT. (As described in D. Gavrilov, B. Gorbovitski, M. Gouzman, G. Gudkov, A. Stepoukhovitch, V. Ruskovoloshin, A. Tsuprik, G. Tyshko, O. Bilenko, O. Kosobokova, S. Luryi, V. Gorfinkel, Electrophoresis 2003, 24, 1184-1192 (hereinafter "Gavrilov et al.").

An exemplary system according to the present invention may have N-channel PMT and M detection lanes. The number of detection lanes may be determined by the number of active capillaries M in the capillary array (M<N). The vector of fluorescence intensities in the capillary lanes may be denoted as $f=(f_1, f_2 \ldots f_M)^T$ and the vector of registered photocount rates as $s=(s_1, s_2 \ldots s_N)^T$, where $(.)^T$ denotes the matrix transpose. The model of the system establishes relationship between f and s vectors:

$$s = \gamma(\epsilon \beta C f + \omega),$$

where $\gamma(.)$ is an operator accounting for non-linearity of the PMT, $\epsilon$ is quantum efficiency of the PMT, $\beta$ is an efficiency of the optical system, $C_{(N \times M)}$ is the cross-talk matrix and $\omega_{(N \times 1)}$ is the noise vector, which defines the stochastic component of s, caused by random arrival times of individual photons and distributed according to Poisson. The quantum efficiency $\epsilon$ determines the percentage of photons that cause the PMT to produce a response on its output. This parameter depends on the wavelength of the fluorescent emission and in our wavelength range it stays below 7%. The efficiency of the optical system $\beta$ is a parameter combining efficiency of the fluorescence collection and delivery systems. In order to simplify the equations, a photocount rate may be defined as a number of photons per sampling interval.

In linear approximation, the cross-talk matrix $C_{(N \times M)}$ combines the electronic and optical cross-talk in the system:

$$C = C^{el} C^{opt}.$$

Electronic Cross-talk

Given the same level of electronic cross-talk between the adjacent channels of the PMT, the matrix $C^{el}_{(N \times M)}$ may take the form:

$$C^{el} = \begin{pmatrix} c_1^{el} & c_2^{el} & & & \\ c_2^{el} & c_1^{el} & c_2^{el} & & \\ & c_2^{el} & c_1^{el} & \ddots & \\ & & \ddots & \ddots & c_2^{el} \\ & & & c_2^{el} & c_1^{el} \end{pmatrix}.$$

Exemplary Cross-talk Matrix 1

In the above Exemplary Cross-talk Matrix 1, the only diagonals containing non-zero elements are the main and two adjacent diagonals, meaning that no electronic cross-talk exists between non-adjacent channels of the PMT. Measurement results confirm that this matrix is valid for analysis of an exemplary system employing the H7260 device described in accordance with FIG. 1. Indeed, the elements of the $C^{el}$ are $c_1^{el}=0.94$ and $c_2^{el}=0.03$, (so that $c_1^{el}+c_2^{el}=1$), and the cross talk level between non-adjacent channels stays negligibly small (below 0.5%).

Optical Cross Talk

Elements of the optical cross-talk matrix $C^{opt}_{(N \times M)}$ depend on the properties of the optical system. In an exemplary embodiment of the present invention, an optical system may include a number of capillaries in the array (number of lanes) equal to the number of channels of the photodetector (M=N), such that $C_{opt}$ is a square matrix of the form:

$$C^{opt} = \begin{pmatrix} c_{11}^{opt} & c_{12}^{opt} & c_{13}^{opt} & & c_{1,N}^{opt} \\ c_{21}^{opt} & c_{22}^{opt} & c_{23}^{opt} & & c_{2,N}^{opt} \\ c_{31}^{opt} & c_{32}^{opt} & c_{33}^{opt} & & c_{3,N}^{opt} \\ & & & \ddots & \\ c_{N,1}^{opt} & c_{N,2}^{opt} & c_{N,3}^{opt} & & c_{N,N}^{opt} \end{pmatrix}$$

Exemplary Cross-talk Matrix 2

Each column of $C^{opt}$ reflects distribution of the fluorescence intensity collected from the corresponding capillary among all N channels of the PMT. The matrix may be normalized as follows:

$$\sum_{i=1}^{N} c_{ij}^{opt} = 1; j = 1 \ldots N.$$

If the number of lanes is smaller than the number of photodetection channels (M<N) and each lane is assigned to its unique primary PMT channel, i.e., the channel to which the most of its fluorescence is forwarded, then the (N×M) matrix is constricted from Exemplary Cross-talk Matrix 2 above by removing the columns with numbers of the PMT channels that do not serve as primary.

Because estimation of the absolute value of the fluorescence intensity is not important in this analysis of the recorded sequencing traces, but rather the relative peak amplitudes are the important consideration, it is convenient to use a vector of 'true' photocount rate $r=(r_1, r_2 \ldots r_M)^T$, which represents the rate that would be obtained in an idealized system, equipped with the ideally linear M-channel estimator of the photocount rate and optical projection system with no cross-talk:

$$r = \epsilon \beta f.$$

According to the above equations, the registered photocount rate s may be related to the 'true' photocount rate as $$s = \gamma(Cr + \omega).$$

The simple minimum variance unbiased (MVU) estimator for r may be found in S. M. Kay, Fundamentals of Statistical Signal Processing. Estimation Theory. Prentice-Hall, N.J., 1993, 597 p., under assumption that the elements of the noise vector in the system are independent, identically distributed random values with Gaussian distribution $N(0, \sigma)$:

where $\hat{r}$ denotes the estimate of r, and $\gamma^{-1}(.)$ is the non-linearity compensation operator applied to the elements of the vector s. The methods for $$\hat{r} = (C^t C)^{-1} C^t \gamma^{-1}(s),$$

characterization and compensation of non-linearity of a single photon detector are described in detail in D. Gavrilov, B. Gorbovitski, M. Gouzman, G. Gudkov, A. Stepoukhovitch, V. Ruskovoloshin, A. Tsuprik, G. Tyshko, O. Bilenko, O. Kosobokova, S. Luryi, V. Gorfinkel, Electrophoresis 2003, 24, 1184-1192, which is incorporated herein by reference in its entirety. If the number of lanes M in the system is equal to the number of photodetection channels, then C is a square (N×N) matrix, and the equation above may be reduced to:

$$\hat{r} = C^{-1} \gamma^{-1}(s).$$

Therefore, in order to find vector $\hat{r}$, information about the cross-talk matrix C must be deduced.

In order to evaluate optical cross-talk, certain assumptions about the characteristics of the optical system which cause the cross talk may be made. A first assumption may be that the optical cross talk in the system is mainly caused by edge aberrations of the lens. Therefore, the cross-talk will depend on the fluorescence collection angle.

In an exemplary embodiment of the present invention, a system using a smaller collection angle may be referred to as Narrow Collection Angle (NCA) system, and a system using a bigger collection angle may be referred to as a Wide Collection Angle (WCA) system. In an NCA system the whole fluorescence collected from each capillary is projected only on the effective space of the corresponding channel of the PMT. The WCA system can not be made to produce a sharp image of the entire capillary array. In an exemplary system according to the present invention, the projected images of the central capillaries of the array may be sharp and may become more and more blurred as the detector is moved closer and closer to the array ends. As a result of blurring, more and more fluorescence is delivered to the nearest neighbors of the designated channels, leading to optical cross-talk between the channels.

Experiments with fluorescence collection using variable aperture show that the NCA approximation for an exemplary optical system is valid when the light collection angle does not exceed 20°. Therefore, the WCA approximation will span all collection angles $20° < \theta < \theta_{max}$, where $\theta_{max}$ is defined either by the lens collection angle or limited to a critical angle of total internal reflection $\theta_C$.

According to Snell's law, $$\theta_C = \sin^{-1}(n_{air}/n_{glass})$$

where $n_{air}$ and $n_{glass}$ are refractive indices of air and glass correspondingly ($n_{air}=1$, $n_{glass}=1.5$, $\theta_C=41.8°$). In the optical system employed in accordance with an exemplary embodiment of the present invention, the lens collection angle is ~45°. Depending on the type of capillary array employed, a different equation may be applied. For example, for capillary arrays which do not include an outer glass box, the collection efficiency may be expressed as:

$$\beta_{max} = \frac{4 n_{glass} n_{air}}{(n_{glass} + n_{air})^2}[1 - \cos(\theta_{max})] = 0.28.$$

For capillary arrays of the type which are immersed into a glass quvette filled with a refractive index liquid, the collection efficiency may be modified and expressed as:

$$\beta_C = \frac{4 n_{glass} n_{air}}{(n_{glass} + n_{air})^2}[1 - \cos(\theta_c)] \approx 0.25$$

Thus, collection efficiencies for both capillary array types are very close. Optical parameter $\beta$ may be denoted as $\beta^{NCA}$ and $\beta^{WCA}$ for NCA and WCA systems correspondingly. Assuming a maximum value of $\beta_{max} \approx 0.25$ and that maximum value of $\beta^{NCA}$ is $\beta^{NCA}(20°)=0.058$, the following may be shown:

$$\beta^{WCA} \approx 4\beta^{NCA}$$

A lane cross-talk removal method in accordance with the present invention may be implemented to remove cross-talk from an NCA system. The NCA system that provides ideally focused image may be described by the diagonal matrix:

$$C^{opt} = diag(1, 1 \ldots 1).$$

Therefore for the NCA system $C = C^{el}$. Due to stability of the electronic cross-talk matrix $C^{el}$, the matrix C can be computed once for the PMT and used until the PMT is replaced.

A lane cross-talk removal method in accordance with the present invention may be implemented to remove cross-talk from a WCA system. In the WCA system, depending on the image quality, the Exemplary Cross-talk Matrix 2 may have non-zero elements on the main and several adjacent diagonals. Analytical evaluation of the matrix C for the WCA system requires evaluation of the $C^{opt}$, which depends on specific design of the optical system and may vary not only from system to system, but even after every replacement of the multi-capillary array because of the system misalignment caused by a finite tolerance of the array positioning system.

Therefore, for determining elements of the C matrix for specific detection system, it is more practical to use a special calibration procedure based on sequencing data obtained from the system calibration experiment. Obviously, the system calibration must be performed each time a new capillary array is installed.

The calibration of a cross-talk cancellation algorithm in accordance with an exemplary embodiment of the present invention includes estimation of the cross-talk matrix. Two approaches may be employed in accordance with an exemplary embodiment of the present invention—static and dynamic approaches to calibration.

Static Approach

This approach to calibration is well suited for photodetection units. Static calibration may be performed at the stage of device manufacturing before the photodetection unit is installed in the system. The n-th column of a cross-talk matrix is obtained by illuminating the n-th pixel (channel) of the photodetector and recording responses at the outputs of each channel. For example, in calibration of a linear array PMT, the illumination of a single channel can be achieved using a low aperture single mode fiber. The fiber may be equipped with a tip lens to narrow the aperture. Before each experiment the background noise levels may be recorded in each channel. The background levels are subtracted from the responses before their values are used to form the columns of a cross-talk matrix.

Dynamic Approach

The dynamic approach may preferably be employed for calibration of a detection system as a whole. The resulting matrix from such calibration combines the internal and external (i.e., electronic and optical) cross-talk. In this approach, the cross-talk matrix is estimated from the results of the experiment. An algorithm for matrix estimation is utilized to extract the cross-talk information from the recorded data set using knowledge about the specific conditions of the experiment. This approach to calibration of the cross-talk cancellation algorithm may be applied in an exemplary fluorescence detection system for multi-capillary electrophoresis in accordance with the present invention.

Estimation of the lane cross talk includes execution of a series of short sequencing runs. The number of runs in the series is determined experimentally as a number of capillaries between two closest lanes with negligibly small cross-talk.

In one exemplary embodiment of the present invention, for calibration of the lane cross-talk an internal lane standard (ILS-600, Promega Corp) may be used. This sample produces a number of well separated peaks in the 580 nm-620 nm wavelength range on a rather low background level (~1,000 count/s) which generates very low photon counting noise (<250 c/s). Thus, since the typical count rate of the detected ILS peaks varies in the range of ~100,000 c/s-50,000 c/s, the system may be calibrated for as low as 1% lane cross-talk with signal-to-noise ratio larger than 1.

In a case when cross-talk affects only adjacent channels, the calibration experiment consists of only two short runs during which the ILS-600 sample is loaded in either odd or even capillaries of the array. Both recorded data sets may also undergo smoothing and background removal. The odd columns of C may be found using the 'odd' data set and the even columns using the 'even' data set. In both data sets the high quality peaks may be detected in each channel that has a loaded capillary assigned to it during the corresponding sequencing run. If J peaks are detected in the channel $n_i$ to which the fluorescence from the i-th lane is primarily projected, then:

$$b_1 = \frac{1}{J} \sum_{j=1}^{J} \frac{A_{n_i-1}[j]}{A_{n_i}[j]}; b_2 = \frac{1}{J} \sum_{j=1}^{J} \frac{A_{n_i+1}[j]}{A_{n_i}[j]},$$

where $A_{ni}[j]$ is the height of the j-th peak in the channel $n_i$ and $A_{ni-1}[j]$ and $A_{ni+1}[j]$ are the heights of the cross-talk induced peaks in the adjacent channels. The height of the peaks may be determined from the data set obtained by removal of baseline from the raw experimental data. The baseline removal is an important step, because the baseline may constitute significant fraction of the recorded raw data value. Then the non-zero elements of the i-th column of C may be expressed as:

$$c_{n,i} = \frac{1}{1+b_1+b_2}; c_{(n_i-1)i} = \frac{b_1}{1+b_1+b_2}; c_{(n_i+1)i} = \frac{b_2}{1+b_1+b_2}.$$

A similar procedure can be used if a larger number of calibration runs is needed.

Notably, the transition from NCA to WCA detection system causes some of the collected fluorescence to be projected on the 'dead' insensitive spaces of the PMT, introducing additional loss in the efficiency of the detector. It has been shown that in an exemplary system using PMT H7260 in accordance with the present invention, the loss in fluorescence does not exceed 20% if cross-talk between adjacent channels stays below 30% (0.3).

The described cross-talk cancellation algorithm assumes that the photodetection unit has strictly linear characteristic, i.e., it produces the output response (in the case of the PMT module it is the rate of shaped electric pulses) that is proportional to the intensity of incident light. The characteristics of real world devices generally are not strictly linear. In many cases a photodetection unit can be calibrated and the calibration results can be used to compensate non-linearity in the experimental data. The compensation can be performed in software or hardware. The algorithms for calibration and compensation of non-linearity are described in detail in Gavrilov et al. After non-linearity compensation the data can be forwarded to the cross-talk cancellation algorithm of the present invention, which will not introduce additional distortions in the data.

The NCA and WCA detection systems analyses assume that the characteristics of the PMT are known precisely and its non-linearity can be perfectly compensated. The detailed description of the methods for characterization of single photon detectors and non-linearity compensation is presented in Gavrilov et al. In analysis we also assume that significant cross-talk exists only between the adjacent channels and does not exceed 30%. The expressions are derived for the case when the number of lanes M is the same as the number of PMT channels N.

A software module may be implemented in accordance with an exemplary embodiment of the present invention to automatically determine the lane cross-talk matrix based on calibration data. The software module may process a series of calibration runs and produce a configuration file of the lane cross-talk matrix coefficients. A set of active lanes (containing sample) may be specified for each calibration run. The cross-talk removal is performed separately on data obtained in each of the four fluorescence spectral bands. The procedure of estimation of the cross-talk matrix in every spectral band may include base-line removal in all 32 channels followed by peak detection.

The module may search for well resolved fluorescence peaks in the active channels and corresponding cross-talk peaks in the neighboring channels. After non-linearity compensation, noise filtering, and base line subtraction have preferably been performed, the peak heights in active and neighboring channels may be determined. The cross-talk coefficients are found as ratios of peak heights in neighboring channels to the peak height in active channels. The coefficients may be further normalized. The determined cross talk matrix may then be applied for further processing of the sequencing data.

Experiments involving the cross-talk cancellation method of the present invention applied to processing of the experimental traces obtained from Internal Lane Standard 600 (Promega Corporation) sequenced in the 16-capillary array (Applied Biosystems Inc.) and detected using our 32-channel DNA sequencing setup showed favorable results.

While there have been described what are believed to be the preferred embodiments of the present invention, those skilled in the art will recognize that other and further changes and modifications may be made thereto without departing from the spirit of the invention, and it is intended to claim all such changes and modifications as fall within the true scope of the invention.

We claim:

1. A method for reducing cross-talk in a multi-channel data acquisition system, which system includes at least a multi-channel photodetector, comprising:
   determining a cross-talk matrix for the system;
   operating the system to detect data, and applying the cross-talk matrix to the detected data to reduce or remove both optical and electrical channel cross-talk in the detected data.

2. The method of claim 1 wherein the cross-talk matrix is determined theoretically using one or more mathematical formulas which characterize the operation of the system.

3. The method of claim 1 wherein the cross-talk matrix is determined experimentally by calibrating the system by applying known input data and observing the resulting output data.

4. The method of claim 1 wherein the cross-talk matrix is determined experimentally by calibrating one or more subcomponents of the system statically before the subcomponent is installed in the system.

5. The method of claim 1 wherein the cross-talk matrix is determined experimentally by calibrating the system dynamically after the system is assembled.

6. The method of claim 1 wherein the detected data is fluorescence radiation.

7. The method of claim 1 wherein the data is detected by all channels of the system simultaneously.

8. The method of claim 1 wherein the data is detected by all channels of the system sequentially.

9. A method for reducing cross-talk in a multi-channel data acquisition system, which system includes at least a multi-channel photodetector, comprising:
   determining a cross-talk matrix for the system: operating the system to detect data, and applying the cross-talk matrix to the detected data to reduce or remove channel cross-talk in the detected data;
   wherein each channel of said multi-channel system detects and distinguishes fluorescence in more than one spectral band.

10. A method for reducing cross-talk in a multi-channel data acquisition system, which system includes at least a multi-channel photodetector, comprising:
    determining a cross-talk matrix for the system; operating the system to detect data, and applying the cross-talk matrix to the detected data to reduce or remove channel cross-talk in the detected data;
    wherein each channel of said multi-channel system detects and distinguishes fluorescence in more than one spectral band;
    wherein the cross-talk reduction is individually performed for each of the spectral bands.

11. A method for reducing cross-talk in a multi-channel data acquisition system, which system includes at least a multi-channel photodetector, comprising:
    determining a cross-talk matrix for the system: operating the system to detect data, and applying the cross-talk matrix to the detected data to reduce or remove channel cross-talk in the detected data;
    wherein each channel of said multi-channel system detects and distinguishes fluorescence in more than one spectral band;
    wherein the cross-talk reduction is individually performed for each of the spectral bands;
    wherein the cross-talk reduction is followed by color deconvolution of said fluorescence.

12. The method of claim 1 further comprising the step of applying a non-linearity compensation algorithm to the detected data.

13. A system for reducing cross-talk in multi-channel data acquisition, comprising: a multi-channel photodetector; a processor, and a memory coupled to the processor and containing instructions which, when executed by the processor, configure the processor to perform steps comprising: determining a cross-talk matrix; operating the system to detect data, and applying the cross-talk matrix to the detected data to reduce both optical and electrical cross-talk in the detected data.

14. The system of claim 13 wherein the cross-talk matrix is determined theoretically using one or more mathematical formulas which characterize the operation of the system.

15. The system of claim 13 wherein the cross-talk matrix is determined experimentally by calibrating the system by applying known input data and observing the resulting output data.

16. The system of claim 13 wherein the cross-talk matrix is determined experimentally by calibrating one or more subcomponents of the system statically before the subcomponent is installed in the system.

17. The system of claim 13 wherein the cross-talk matrix is determined experimentally by calibrating the system dynamically after the system is assembled.

18. A system for multi-capillary data acquisition comprising; a light source; at least one multi capillary array positioned to receive light from the light source and filled with a material which produces a useful radiation caused by illumination with said light source; a device for separating and identifying more than one spectral band of said useful radiation; a multi channel photodetector positioned to receive said useful radiation from the multi capillary array; a processor configured to receive data originating from the photodetector and a memory coupled to the processor and containing instructions which, when executed by the processor, configure the processor to perform steps comprising: determining a cross-talk matrix; operating the system to detect fluorescence data, and applying the cross-talk matrix to the fluorescence data to reduce both optical and electrical cross-talk in the fluorescence data.

19. The system of claim 18 wherein the cross-talk matrix is determined theoretically using one or more mathematical formulas which characterize the operation of the system.

20. The system of claim 18 wherein the cross-talk matrix is determined experimentally by calibrating the system by applying known input data and observing the resulting output data.

21. The system of claim 18 wherein the cross-talk matrix is determined experimentally by calibrating one or more subcomponents of the system statically before the subcomponent is installed in the system.

22. The system of claim 18 wherein the cross-talk matrix is determined experimentally by calibrating the system dynamically after the system is assembled.

23. The system of claim 18 wherein the data is detected by all channels of the system simultaneously.

24. The system of claim 18 wherein the data is detected by all channels of the system sequentially.

25. The system of claim 24 wherein the cross-talk reduction is individually performed for each of the spectral bands.

26. The system of claim 18 wherein each channel of said multi-channel system detects and distinguishes fluorescence in more than one spectral band.

27. The system of claim 26 wherein the cross-talk reduction is followed by color de-convolution of said fluorescence.

28. The system of claim 18 which perform multicolor DNA sequencing.

29. A method for determining a cross-talk matrix for a multi-capillary data acquisition system, comprising: applying an input sample to a first capillary; detecting fluorescence at a first channel which corresponds to the first capillary and at least a second channel; recording the detected fluorescence data; processing the recorded data from the first and the second channels to determine what fraction of the fluorescence from the input sample was received by the first channel and what fraction of the fluorescence from the input sample was received by the second channel, and recording the determined fractions in a column of the cross-talk matrix.

30. The method of claim 29 further comprising the step of isolating at least a third channel from fluorescence emitted from at least a second capillary.

31. The method of claim 30 wherein the fluorescence from the second capillary is isolated using a mask.

32. The method of claim 29 where the input sample produces a fluorescence signal with a specific signature which distinguishes this signal from other photo-signals in the data acquisition system.

* * * * *

UNITED STATES PATENT AND TRADEMARK OFFICE
CERTIFICATE OF CORRECTION

| | |
|---|---|
| PATENT NO. | : 7,402,817 B2 |
| APPLICATION NO. | : 11/627146 |
| DATED | : July 22, 2008 |
| INVENTOR(S) | : Dimitri N. Gavrilov et al. |

It is certified that error appears in the above-identified patent and that said Letters Patent is hereby corrected as shown below:

IN THE SPECIFICATION:
On Page 1, Column 1, line 11, please insert the following header and paragraph:

-- Statement Regarding Federally Sponsored Research or Development
This invention was made with government support under grant number HG002575 awarded by the National Institutes of Health. The government has certain rights in the invention. --

Signed and Sealed this

Seventh Day of October, 2008

JON W. DUDAS
*Director of the United States Patent and Trademark Office*